United States Patent [19]
Wehrli et al.

[11] Patent Number: 4,777,957
[45] Date of Patent: Oct. 18, 1988

[54] METHOD FOR MEASURING AND IMAGING FLUID FLOW

[75] Inventors: Felix W. Wehrli, Shorewood; Ann Shimakawa, Milwaukee, both of Wis.

[73] Assignee: General Electric Company, Milwaukee, Wis.

[21] Appl. No.: 744,926

[22] Filed: Jun. 14, 1985

[51] Int. Cl.$^4$ .............................................. A61B 5/05
[52] U.S. Cl. ..................................... 128/653; 128/696; 324/306; 324/309
[58] Field of Search ...................... 128/653, 696, 708; 324/306, 309

[56] References Cited

U.S. PATENT DOCUMENTS

| | | | |
|---|---|---|---|
| 4,409,550 | 10/1983 | Fossel et al. | 324/300 |
| 4,413,233 | 11/1983 | Fossel et al. | 324/300 |
| 4,431,968 | 2/1984 | Edelstein et al. | 324/309 |
| 4,516,582 | 5/1985 | Redington | 128/653 |
| 4,528,985 | 7/1985 | Macouski | 128/653 |
| 4,532,473 | 7/1985 | Wehrli | 128/653 |
| 4,570,119 | 2/1986 | Wehrli et al. | 324/306 |
| 4,602,641 | 7/1986 | Feinberg | 128/653 |

OTHER PUBLICATIONS

Wedeen et al., "Projective Imaging Of Pulsatile Flow With Magnetic Resonance", *Science*, vol. 230: pp. 946–948; 1985.

J. R. Singer et al., "NMR Blood Flow Measurements in the Human Brain"; *Science*, Aug. 12, 1983, vol. 221 pp. 654–656.

F. W. Wehrli et al., "Approaches to In-Plane and Out-of Plane Flow Imaging"; *Noninvasive Medical Imaging*, Apr. 1984, vol. 1, No. 2: 127–136.

P. A. Bottomley, "NMR Imaging Techniques and Applications: A Review"; *GE Technical Information Series* Aug. 1981; Report No. 81 CRD 195.

I. L. Pykett, "NMR Imaging in Medicine"; *Scientific American*, May 1982 pp. 78–88.

Delayre et al., "Gated Sodium-23 Nuclear Magnetic Resonance Images of an Isolated Perfused Working Rat Heart", *Science*, vol. 212 No. 4497 22 May 1981 pp. 935–936.

*Primary Examiner*—Ruth S. Smith
*Attorney, Agent, or Firm*—Leydig, Voit & Mayer

[57] ABSTRACT

A time-of-flight magnetic resonance pulse sequence is used to detect arterial flow in an image of a slice of tissue. By timing the pulse sequence with the cardiac cycle and by holding the interpulse interval $T_I$ within time limits which ensure enhancement without significant change in flow velocity, arterial flow can be imaged. By triggering the pulse sequence from the QRS complex representative of the beginning of a body's cardiac cycle and delaying both excitation and detection pulses in the sequence by a time $T_A$ to ensure the pulses occur while flow is slow, MR signal data is generated which results in an image showing enhancement in the areas of arterial flow. In an extension of the foregoing, a second set of MR signal data is generated by adjusting the acquisition delay $T_A$ such that the excitation and detection pulses of a second sequence occur while arterial flow is fast. In the image formed from this second set of data, the increased arterial flow velocity decreases the enhanced image of the arteries. The images generated from the MR signals of the first and second sequences may be subtracted in order to give a single high contrast image showing only arterial flow.

14 Claims, 5 Drawing Sheets

METHOD FOR MEASURING AND IMAGING FLUID FLOW

TECHNICAL FIELD

This invention generally relates to an apparatus and method utilizing magnetic resonance (hereinafter referred to as "MR") techniques for enhancing the image produced from MR data of a flowing fluid and, more particularly, for enhancing the image of a flowing fluid having a time-dependent velocity.

BACKGROUND

Magnetic resonance imaging has a number of capabilities and attributes that distinguish it from other diagnostic modalities. In addition to its potential ability to monitor cell metabolism on a molecular level, an important feature of the MR signal is its sensitivity to bulk motion such as blood flow in living tissue. Depending on the specific pulse scheme used and on the nature of the pulses administered, the image of flowing fluid may be either enhanced or reduced in intensity relative to a stationary ambient environment. The flow dependence of the MR signal is one of MR's unique properties whose exploitation for the study of the cardiovascular system has only recently begun.

Many approaches have been proposed for measuring or imaging flow. One group of MR methods for imaging flow are commonly referred to as time-of-flight methods. In one well-known time-of-flight method, a selective saturation recovery spin echo pulse sequence (hereinafter referred to as "SSRSE") is utilized to provide images which are enhanced in the area of flow. Although this method has proven highly successful in imaging venous flow, this method and others fail to satisfactorily distinguish arterial flow from its surrounding stationary tissue. Apparently, the pulsatile nature and high velocity of flow in arteries (resulting from flow surges caused by cardiac contractions) severely impairs refocusing the spins associated with the microscopic magnetic moments caused by the slice-selection magnetic gradients applied during MR imaging. The impairment of refocusing by flow effects leads to irreversible dephasing of the spins. Because refocusing of the spins is severely impaired by fast flow, the image from arterial flow is not necessarily of enhanced intensity as is slower, venous flow and, therefore, arterial flow may not be distinguishable from surrounding stationary tissue. A further complication is the circumstance that arterial flow is pulsatile, i.e., the flow velocity varies over the cardiac cycle.

Because of the lack of known methods to specifically image arterial flow, the MR image has been unable to give a reliable indication of the nature of a particular vessel. Since arterial stenosis from atherosclerotic buildup is a common pathological condition and since cardiovascular disease is the major cause of death in this country, an accurate image of arterial flow is important. Moreover, arterial stenosis commonly does not become symptomatic until it is life threatening. Because early detection of arterial stenosis may allow treatment of the blockage with drugs or other means less radical than surgery, early detection of abnormalities in arterial flow is diagnostically important.

SUMMARY OF THE INVENTION

In view of the foregoing, it is the primary object of the present invention to provide a method for accurately imaging arterial flow using MR techniques. In this connection, it is a related object of this invention to provide a method for imaging arterial flow using MR techniques such that the arterial flow is distinguishable from venous flow.

It is another object of the invention to provide a method for creating a single MR image showing only arterial flow.

Other objects and advantages of the invention will be apparent from the following detailed description and the accompanying drawings.

In accordance with the invention, a plurality of microscopic magnetic spins in a first slice of tissue, which is preferably substantially perpendicular to the direction of fluid flow, are tagged (preferably, but not necessarily, saturated, i.e., their magnetization rotated into the transverse plane) in a timed relationship with the cardiac cycle and then excited to produce a first MR signal. In order to ensure arterial enhancement, a pulse sequence is utilized with an interpulse interval $T_I$ which is short enough to ensure the flow is substantially constant and yet long enough to achieve satisfactory enhancement (typically 50 to 100 ms). By timing the pulse sequence with the cardiac cycle and by holding the interpulse interval $T_I$ within time limits which ensure enhancement without significant change in flow velocity, arterial flow can be imaged. By triggering the pulse sequence from the QRS complex representative of the beginning of a cardiac cycle and delaying both excitation and detection pulses in the sequence to ensure they occur while flow is slow, MR signal data is generated which results in an image showing enhancement in the areas of arterial flow. The specific value of the delay $T_A$ for the excitation and detection pulses (measured from the beginning of a cardiac cycle to the start of the pulse sequence) depends on the location of the imaging slice relative to the heart. Therefore, the value for $T_A$ must be determined empirically. In an extension of the foregoing, a second set of MR signal data is generated by adjusting the acquisition delay $T_A$ such that the excitation and detection pulses of a second sequence occur while arterial flow is fast. In the image formed from this second set of data, the increased arterial flow velocity lowers arterial signal intensity. The images generated from the MR signals of the first and second sequences may be subtracted in order to give a single high contrast image showing only arterial flow.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

FIGS. 6a-e is a schematic timing diagram illustrating the synchronization of the MR pulse sequence with the cardiac cycle and the corresponding slow and fast blood flow in accordance with the invention;

For MR imaging to monitor flow by a time-off-light method, it is a well-known requirement that there be a finite component of the flow velocity perpendicular to the imaging plane. For purposes of clarity, the simplest case of total perpendicular flow through the imaging plane is assumed in connection with the description of the preferred embodiment of the invention.

DETAILED DESCRIPTION OF THE PREFERRED EMBODIMENT

Figure 1:
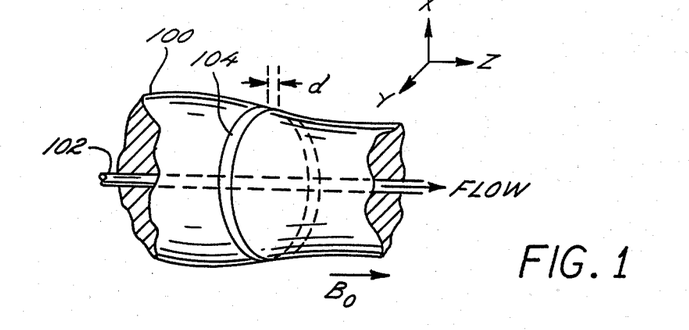
FIG. 1 illustrates an MR sample situated in a substantially homogeneous magnetic field and having a sample slice defined therein by a selective RF pulse sequence and pulsed field gradients for studying arterial flow in accordance with the invention.

Referring first to FIG. 1, a sample 100, composed of living tissue, is situated in a substantially homogeneous magnetic field $B_0$ directed in the positive Z-axis direction of a Cartesian coordinate system which is generally parallel to the direction of blood flow within a vessel 102 in the sample. In response to the applied magnetic field $B_0$, the microscopic magnetic moments in the slice 104 tend to line up with the field along the Z-axis. As a result of the alignment of the microscopic moments, a macroscopic moment is created which is commonly referred to as the net magnetization, M (not shown), parallel with the magnetic field $B_0$. When exposed to a magnetic field each microscopic magnetic moment experiences a precessional frequency given by the Larmor equation, $f = \gamma/2\pi B_0$ where $\gamma$ is the magnetrogyric ratio the particular nuclei selected.

Figure 2:
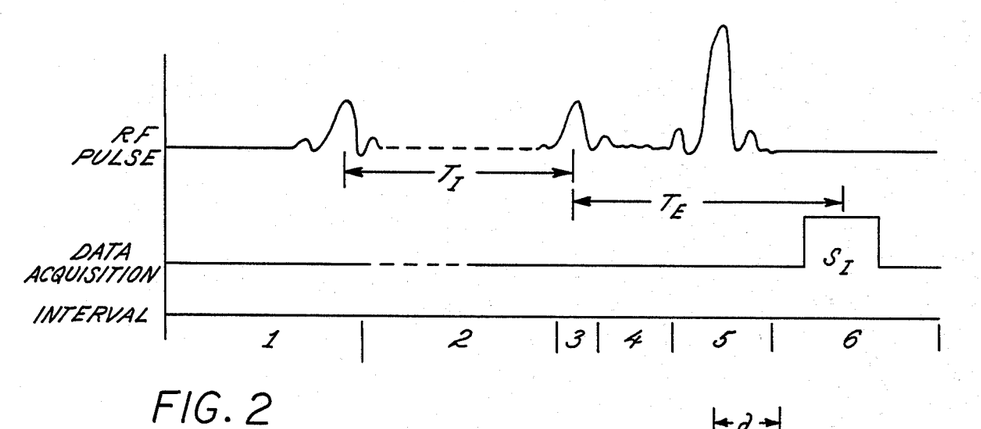
FIG. 2 depicts a generalized MR pulse sequence used in selecting the sample slice depicted in FIG. 1 in accordance with the invention.
Figures 3A, 3B:
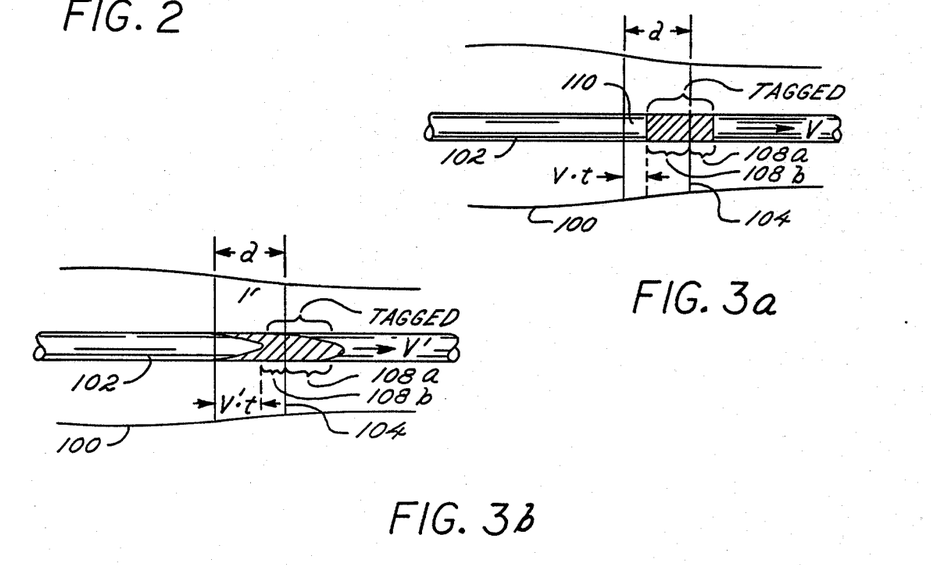
FIG. 3a schematically depicts the distribution of a bolus of blood through the selected sample slice of FIG. 1 after a time period t from the time of the tagging pulse, assuming a flow wherein the blood moves uniformly through the vessel, much like a moving plug.
FIG. 3b schematically depicts the distribution of a bolus of blood through the selected sample slice of FIG. 1 after a time period t from the time of the tagging pulse, assuming a distribution of flow velocities in such a manner that fluid molecules near the wall have lower velocities than those near the center of the blood vessel.

Referring now to FIGS. 1, 2, and 3a, the microscopic spins in a transverse slice 104 of the sample 100 are perturbed by the application of a selective 90° RF perturbation pulse (as shown in interval 1 of FIG. 2) along with a Z gradient (not shown) so as to redirect the net magnetization, M, for that slice to a direction transverse from the magnetic field $B_0$. In order not to interfere with the signal generated by the second 90° pulse, the transverse magnetization created by the initial 90° RF pulse is dispersed by a dephasing gradient (not shown) along the Z-axis, applied following the slice-selection gradient (also not shown). The effect of the perturbation utilizing the 90° RF pulse and the dephasing gradient is to first rotate the net magnetization into the X-Y plane (i.e., the transverse plane) and then to destroy any macroscopic transverse magnetization by dephasing the spins of the microscopic magnetic moments which comprise the net magnetization M. Hereinafter, nuclei which have been perturbed, as described above, will be referred to as the "tagged" nuclei. Since the object of the pulse in interval 1 of FIG. 2 is to tag the flowing nuclei, it will be appreciated that selective pulses of flip angle $\theta \neq 90°$ may alternatively be used to perturb the net magnetization M in place of the 90° pulse shown in FIG. 2.

Following the perturbation pulse in interval 1 of FIG. 2, the magnetic moments of the tagged nuclei are allowed to partially recover during interval 2 and begin to realign with the field $B_0$ to create a net longitudinal magnetization component in a positive Z-axis direction whose final magnitude depends on the length $T_I$ of interval 2 and the spinlattice relaxation time $T_1$ of the fluid protons. During the recovery period, the tagged nuclei which were orignally in imaging slice 104, indicated by shaded areas 108a and 108b in FIG. 3a, are partially or fully replaced by unperturbed (untagged) nuclei as indicated by area 110. Thus, when a second selective 90° pulse is applied in interval 3 of FIG. 2, the total net magnetization generated by the pulse is the sum of the partially recovered longitudinal magnetization of the tagged nuclei remaining in slice 104 (shown as shaded area 108b) from the first pulse and the net longitudinal magnetization attributable to the previously untagged nuclei (area 110).

In interval 5, a slice-selective 180° pulse is applied which generates a spin echo $T_E$ milliseconds after the second 90° pulse. The time period $T_E$ is commonly referred to as echo delay. The foregoing pulse sequence will henceforth be referred to as a selective saturation recovery spin echo or SSRSE sequence. In interval 6, the spin echo signal $S_I$ is sampled to provide data for reconstruction of the image. It represents a signal attributable to the tagged spins in the slice (stationary and flowing), as well as the untagged spins which have entered the slice (flowing only). For slow flow, signal $S_I$ is more intense than it would be in the absence of flow, due to the transverse magnetization contributed by the untagged spins.

The second slice-selective 90° pulse (detection pulse, interval 3), administered $T_I$ milliseconds after the first pulse, creates transverse magnetization which arises from the spins of the microscopic magnetic moments remaining in the slice 104 from the first slice-selective pulse (area 108b) and spins that have entered the slice since that time (area 110). For a slice thickness d, a spin-lattice relaxation time $T_1$ and a flow velocity v, the signal component generated by spins that have experienced both pulses is given by $(1 - vT_I/d)(1 - e^{T_I/T_1})$. The spins moving into the imaging slice between tagging and detection pulse are assumed to be fully magnetized with the resulting signal proportional to $vT_I/d$. Hence, when ignoring the effect of the 180° refocusing pulse, the relative MR signal intensity I can be expressed as:

$$I = k\{vT_I/d + (1 - vT_I/d)(1 - e^{-T_I/T_1})\} \quad (1)$$

where k is a proportionality constant, which is independent of flow and relaxation time characteristics. Equation (1) is valid within the boundaries $$0 < vT_I < d \quad (2)$$

It should further be noted that at $vT_I = d$, the signal cannot grow any further since all spins have been replaced and the signal assumes a limiting value (final amplitude) $I^{lim}=k$. On the assumption that the relaxation time $T_1$ is much greater than $T_I$, the signal intensity increases for increasing values of $T_I$, ultimately reaching a plateau for the limiting condition where $T_I=d/v$.

The prediction in Equation (1) that signal intensity steadily increases with increasing interpulse interval $T_I$ until the interval equals the transit time has been verified in phantom flow (i.e., flow of doped water through, for example, tygon tubing) and has served as the basis to measure the flow velocity of blood in venous structures such as the femoral vein. But, it has also been shown that the final intensity of a pixel in an image, attained when $T_I$ equals the transit time, decreases with increasing flow velocity; an effect which cannot be explained by the influx of untagged nuclei.

Figure 4:
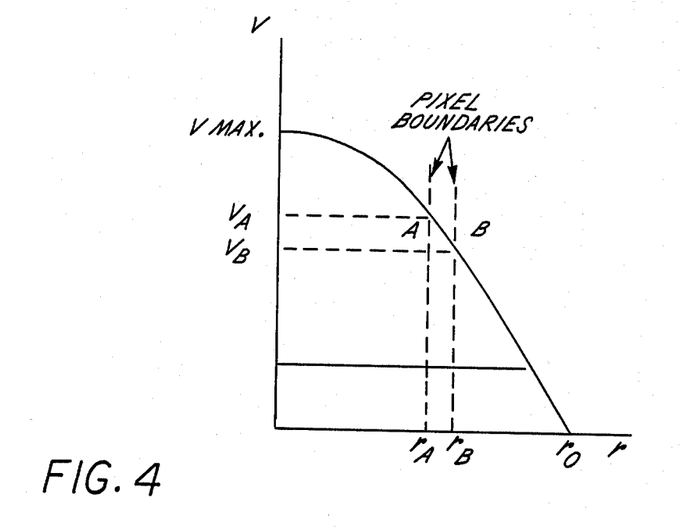
FIG. 4 is a graph illustrating the relative radial velocities of the bolus of tagged fluid across the pixel boundaries for an MR image wherein the fluid has a parabolic velocity distribution between velocities $V_A$ and $V_B$.
Figure 5:
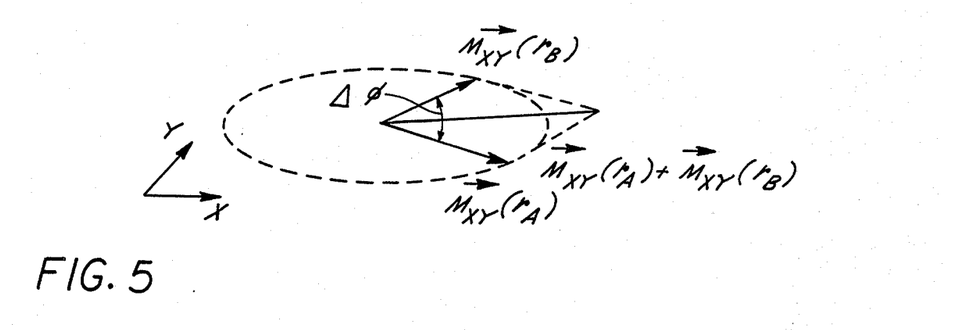
FIG. 5 is a vector representation of the dephasing occurring within the boundaries of the pixel identified in FIG. 4.

Two circumstances account for a diminution of the final signal intensity as the flow velocity increases. The first circumstance is the entry into the slice of spins during interval 4 (FIG. 2) These spins have not sensed the second 90° pulse in interval 3 and thus do not contribute to the signal; in fact, they cause a reduction in signal intensity which is proportional to $v \cdot T_E/(2d)$. Hence, in the extreme case where $v \cdot T_E = 2d$ the signal vanishes. The threshold velocity at which the signal vanishes, sssuming for example $T_E = 25$ ms and $d=1$ cm, is 80 cm/s. The second circumstance is the fact that rather than behaving like a moving plug, fluid has a radial velocity distribution as indicated in FIG. 3b and 4. This intralumenal velocity gradient causes phase shifts of the microscopic magnetic moments making up the macroscopic magnetization (FIGS. 4 and 5). The effect becomes more important as the flow velocity increases. These phase shifts lead to destructive interference of the magnetic moments and thus a reduction in signal intensity. Consequently, the MR signal from fast flowing blood is reduced in its intensity relative the slower flowing blood. Therefore, as blood flow increases in velocity as it does in arteries, the dephasing effect caused by the radial flow velocity gradient accentuates and the associated dephasing of the spins becomes a significant factor affecting signal intensity.

Referring to FIG. 4, flow through a vessel is characterized by a flow distribution wherein the velocity of the flowing fluid varies from a maximum, $V_{max}$ at the center of the vessel to zero, at the walls of the vessel. During MR imaging, the velocity of the flow affects the phase of the magnetic moments of particles in the flow. Therefore, the unequal velocities of the flow causes a dephasing of the microscopic magnetic moments which add to form a net magnetic moment for the vessel. For example, if a pixel of the image for the vessel extends from A to B in FIG. 4, then the particles at the pixel extremes have positions $r_A$ and $r_B$ and velocities $v_A$ and $v_B$, respectively. Referring briefly to FIG. 5, it can be shown that in the case of constant gradient amplitude, the spins of the magnetic moments of the particles in radial positions $r_A$ and $r_B$ are out-of-phase by an amount equal to $\Delta\phi$ such that $$\Delta\phi = \gamma G_z(v_A - v_B)\tau^2/2 \quad (3)$$

where $\gamma$ is the magnetrogyric ratio, $G_z$ is the magnetic gradient along the z-axis, $\tau$ is the total magnetic gradient duration and $v_A$ and $v_B$ denote the flow velocity at radial positions $r_A$ and $r_B$, respectively. As can be seen in FIG. 5, the resultant voxel magnetization has decreased magnitude because of the phase difference of the magnetic moments making up the voxel. Therefore, the final amplitude $I^{lim}$ of the signal (i.e., the amplitude reached when $T_I \geq T_{TR}$, where $T_{TR}$ is the mean transit time) is not really a constant k as implied by equation (1) where the flow velocity was assumed to be independent of position. Instead, it is a function of flow velocity, echo delay $T_E$, gradient amplitude and duration and, most importantly, as is evident from FIG. 4, the velocity gradient $\partial v/\partial r$ across the pixel under consideration.

In the case of slow flow in a vessel, such as blood flow through a vein, the velocity gradient $\partial v/\partial r$ across the pixel boundaries A and B is relatively small. Therefore, the reduction of the net magnetic moment for the pixel caused by dephasing is not significant. As a result of no significant dephasing in slow flow, image enhancement from the imaging sequence outlined in connection with FIGS. 1–3a is relatively unaffected. In contrast, arterial flow includes intervals of both slow and fast flow. During the fast flow, the velocity gradient $\partial v/\partial r$ across the pixel boundaries A and B becomes appreciable (see FIG. 3b). Consequently, the dephasing of spins significantly reduces the net magnetization M within the pixel, thereby causing a corresponding significant reduction in enhancement of the arterial flow image. In fact, arterial signal intensity is often so low that it is difficult to distinguish from other low-intensity signals such as those arising from muscle tissue.

Arterial flow is not only much faster on the average than venous flow, it is also pulsatile, i.e., the flow rate varies throughout the cardiac cycle. The fast arterial flow and its pulsatile nature explain the very low signal intensity for arterial flow observed with virtually all imaging techniques.

In accordance with the invention enhancement of arterial flow is made possible for MR imaging methods such as time-of-flight based spin-echo imaging methods such as SSRSE by synchronizing data acquisition to the cardiac cycle and by choosing an appropriate delay $T_A$ of data acquisition after the occurrence of an event in the cardiac cycle to which data acquisition is synchronized. In a series of images obtained in the SSRSE mode wih gating of the initiation of the pulse sequence to the QRS complex of the cardiac cycle at a fixed interpulse interval and variable acquisition delays $T_A$, and MR signal intensity pertaining to an artery varies as a function of acquisition delay. By contrast, the intensity of the veins within the slide is essentially independent of acquisition delay. Therefore, the invention permits imaging which discriminates between arterial and venous structures. Because the occurrence of fast flow in an artery depends on its position relative to the heart, the acquisition delay affording optimum arterial signal enhancement has to be evaluated empirically. In determining the appropriate acquisition delay, the propagation velocity of fast flow in response to a cardiac contraction must be considered as well as the distance of the imaging slice from the heart.

In keeping with the invention, the foregoing approach is used in connection with subtracted images collected by the same SSRSE sequence but differing in their acquisition delays $T_A$. For example, for an arterial flow image in a human thigh obtained by subtracting from one another the gated SSRSE images collected with $T_A=1$ ms and $T_A=300$ ms, the two images comprise MR signals gathered at different arterial flow velocities; therefore, the images exhibit significant differences in the degree of arterial signal enhancement.

But, for venous flow, the enhancement of the MR signals is the same in both images. Likewise, stationary tissue protons provide signal intensity that are independent of the acquisition delay $T_A$. Therefore, subtraction of the images leaves only the arterial flow. Such an image can be easily inspected to determine flow velocity in the artery (degree of enhancement) and the extent of arterial blockage (area of image), if any.

Figure 6:
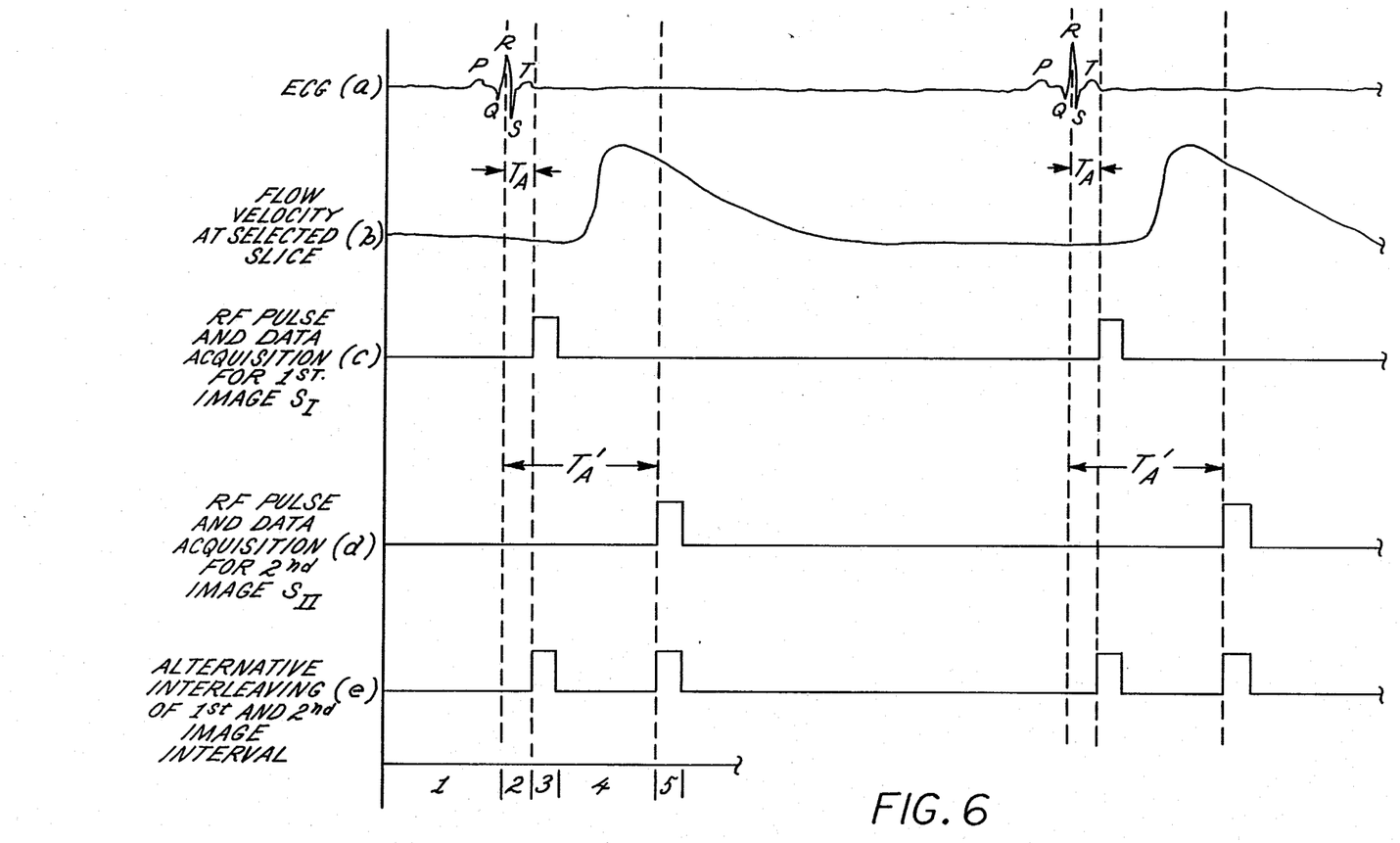
Figure 7:
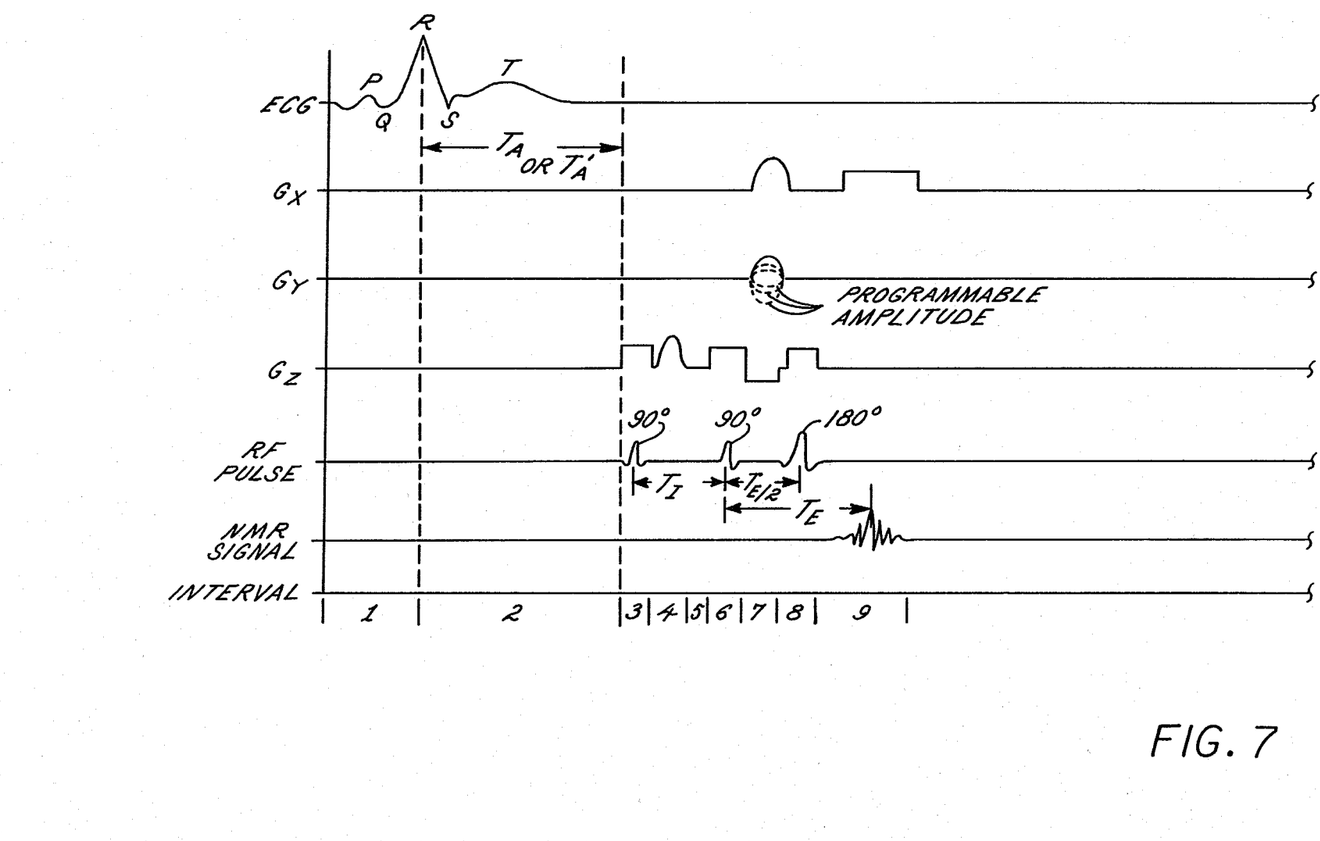
FIG. 7 is a detailed MR pulse sequence utilized in accordance with the invention to enhance arterial blood-flow using the spin-warp imaging method.

The manner in which the method of the invention may be utilized to obtain images of an object depicting blood flow will be undertaken with reference to FIGS. 6 and 7. In order to simplify FIGS. 6 and 7, the homogeneous magnetic field $B_0$ is not separately depicted in each of these figures; the field gradients are, however, illustrated in FIG. 7.

In the preferred embodiment, the invention, which is described in general terms with reference to FIG. 6, is preferably practiced with the pulse sequence depicted in FIG. 7 and which is known as spin-warp imaging. Spin-warp imaging is a special case of the two-dimensional Fourier transform (2DFT) phase-encoding method of MR imaging. Typically, in spin-warp imaging, a series of projections is obtained by sampling a signal m times and repeating this process for n different values of the phase encoding gradient. Usually a spin echo is created which is collected at $t=T_E$ following the 90° detection pulse. According to the invention, all pulses have to be selective (i.e., narrow-banded), and it is basically a saturation-recovery pulse sequence, which consists of a saturation pulse (first 90° pulse) for tagging the nuclei and a detection sequence comprising a second 90° pulse, followed by a 180° refocusing pulse as previously described.

In the timing diagrams of FIGS. 6a–e, the invention is described in general terms such that the RF pulse sequence and the responsive MR signal are symbolized by a single square wave pulse in order to indicate the relative location in time of the pulse sequence and data acquisition with respect to blood flow. Because the cardiac cycle is directly related to the cycle of arterial blood flow, the MR pulse sequence is as a practical matter referenced to the electrical potential of the heart. An MR image having a distinct intensity for arterial flow is provided by gating the RF pulse sequence and the associated data acquisition to the cardiac electrical potential or ECG signal such that the pulse sequence and acquisition data occur at a predetermined time in the cycle of arterial flow between slow and fast flow. Although two successive cycles of arterial flow are shown in FIGS. 6a–e to illustrate the cyclic nature of the flow, only the first cycle will be discussed in detail.

The electrical potential of the heart appears in a three-component complex, P, QRS and T in FIG. 6a. The P-wave (interval 1) corresponds to the electrical potential of the SA node of the heart which initiates a cardiac cycle. The QRS-waveform (intervals 1 and 2) generally corresponds to the ventricular contraction which initiates the propagation of fast flow through the artery. Ventricular relaxation is generally associated with the T-wave (intervals 3 and 4). Because the R-wave of the QRS-waveform is the most distinct wave in the ECG signal and because it is directly related to the cyclic period for the pulsatile flow in an artery, the synchronization of the SSRSE sequence is preferably based on the R-wave. The occurrence of the R-wave triggers the beginning of an acquisition cycle by first delaying for the time period $T_A$ or $T_A$, in FIGS. 6b or 6d, respectively. Because the fast flow of blood in response to cardiac contraction propagates through the body, the pulsatile flow in the slice encompassing the artery to be imaged is synchronized with the cardiac cycle but exhibits a phase-delayed relationship with the cycle which is dependent upon the distance of the imaging slice from the heart. In order to compensate for propagation delay so the MR pulse sequence and data acquisition occur at the desired point in the blood flow cycle, the acquisition delay $T_A$ is provided.

By selecting an appropriate delay $T_A$ (interval 2) between the detection of an R-wave and the triggering of the imaging pulse sequence (interval 3), MR signals $S_I$ for an entire image can be gathered during slow arterial flow as indicated by FIGS. 6ac. Without synchronization of the acquisition of MR signals to blood flow velocity, the MR signals will occur randomly throughout a blood flow cycle, thereby resulting in a noticeable reduction in image enhancement for arterial flow because of the aforementioned dephasing occurring in MR signals taken during fast flow. By synchronizing the MR pulse sequence to the slow velocity period of an arterial flow cycle, the effect of dephasing the spins caused by the radial flow distribution is diminished, and therefore, the SSRSE time-of-flight pulse sequence provides an image showing enhancement in the area of arterial flow.

In contrast to the enhanced image obtained by synchronizing data acquisition with slow arterial flow, an arterial image of reduced intensity is obtained when the RF pulse sequence and data acquisition occur at a time of fast flow. With an acquisition delay $T_A'$ (intervals 2, 3 and 4), the data acquisition signal $S_{II}$ for an image occurs during a time of fast flow (interval 5) and, therefore, a time of relatively large dephasing of spins.

Because of the different location in the flow cycle of data acquisition, the first and second images will be characterized by different arterial signal amplitude. Because other areas are stationary or have constant, non-cyclical flow (such as veins), the subtraction of one image from the other, $S_I-S_{II}$, will yield a single image showing only regions of arterial flow. This difference image gives an easily interpretable qualitative indication of arterial flow and arterial area (size of vascular lumen).

As an alternative to the sequential collection of full sets of $S_I$ and $S_{II}$ data, the data collection may be interleaved as suggested in FIG. 6e. Assuming a satisfactorily accurate refocusing pulse is available, the collection of $S_I$ and $S_{II}$ data can occur in the same blood flow cycle. By interleaving the acquisition of $S_I$ and $S_{II}$ data, the time required to generate two full images having different acquisition delays $T_A$ and $T_A'$ can be cut in half.

Turning to the detailed illustration of the SSRSE pulse sequence in FIG. 7 which is preferred in this invention, intervals 1 and 2 include the P, QRS and T waveforms of the cardiac cyle discussed in connection with FIGS. 6a–e. Interval 2 corresponds to the acquisition delay $T_A$ or $T_A'$ of FIG. 6 such that the SSRSE pulse sequence begins a time period $T_A$ or $T_A'$, respectively, after the detection of the R-wave. In interval 3, a sample is subjected to a magnetic field gradient $G_z$ and is simultaneously exposed to a selective 90° RF pulse. The RF pulse is preferably modulated, as indicated schematically in FIG. 7, by a sinc (Sin x/x) function to contain a limited band of frequencies selected as predicted by the Larmor equation to rotate macroscopic magnetization M into the transverse plane in imaging slice 104 (FIG. 1). Dephasing of the microscopic magnetic moments whose net macroscopic magnetization M has been rotated into the transverse plane in interval 3 is achieved in interval 4 by the application of a second magnetic field gradient $G_z$, such that by the end of interval 4 the net transverse magnetization in the transverse plane has been destroyed. Hence, a MR signal is not observed at this point. In interval 5, the longitudinal component of magnetization M is allowed to partially recover (i.e., the spins partially realign with the $B_0$ magnetic field) in accordance with the spinlattice relaxation time $T_1$. In interval 6, a second selective 90° RF pulse, or detection pulse, is applied in the presence of a pulsed magnetic field gradient $G_z$ to rotate into the transverse plane both the partially recovered longitudinal magnetization component of the tagged nuclei remaining in detection slice 104 and the net magnetization of the untagged nuclei which have entered the slice since the first RF pulse of the sequence.

The direction of the magnetic field gradient $G_z$ is reversed and its magnitude halved in interval 7 to rephase the magnetic moment rotated by the RF pulse applied in interval 6. Also during interval 7, a phase-encoding gradient $G_y$ is applied simultaneously with the application of a pulsed gradient $G_x$. In each successive sequence, a different peak amplitude (as implied by the dashed lines indicated in interval 7) of the $G_y$ phase-encoding gradient is selected. The gradient $G_y$ encodes spatial information in the Y-axis direction by introducing a twist in the orientation of the transverse magnetization by a multiple of $2\pi$ over the total length of sample 100 (FIG. 1) in the Y-axis direction. Following the application of the first phase-encoding gradient $G_y$, the transverse magnetization is twisted into a one-turn helix. Each different amplitude of the gradient $G_y$ introduces a different degree of twist (phase encoding). The number of $G_y$ gradient amplitudes is chosen to be equal to the number of pixels (typically 128 or 256) the reconstructed image will have in the Y-axis direction. In practice, the signals may be averaged several times prior to advancing the $G_y$ gradient in order to improve the signal-to-noise ratio.

The effect of the $G_x$ gradient in interval 7 is to dephase the microscopic magnetic moments by a predetermined amount so as to correctly time the spin-echo signal $S_I$. When a 180° RF pulse is applied in interval 8, the spin-echo signal $S_I$, having an intensity I', will be obtained in interval 9. The spin-echo signal $S_I$ will occur at a time following the mean application of the 180° RF pulse which is one half the time $T_E$ between the mean application of the 90° RF pulse in interval 6 and the spin-echo signal, (provided the time integral of the waveform of gradient $G_x$ over interval 7 is selected to be equal to the time intergral of the waveform of gradient $G_x$ over interval 9). Spatial information is encoded in the X-axis direction by the application of linear $G_x$ gradient in interval 9 causing the microscopic spins to resonate at frequencies characteristic of their location with respect to the X-axis. The $S_I$ signal is sampled a number of times equal to the number of pixels (typically 128 or 256) the reconstructed image will have in the X-axis direction. The image pixel values are obtained from the sampled signals using a two-dimensional Fourier transform, as disclosed, for example, by Kumar et al. in *J. Mag. Res.* Vol. 18, p. 69 (1975).

The pulse sequence comprising intervals 2 through 9 depicted in FIG. 7 is repeated, changing the amplitude of gradient $G_y$ in interval 7 each time, to obtain a plurality of spaced projections each separated by angle $\Delta\theta$ so as to cover at least a 180° arc in an imaging slice as exemplified by slice 104 in FIG. 1. The MR signals are sampled for each projection, Fourier transformed and stored in an electronic memory of the MR apparatus of FIG. 8 for later use. Fourier transformation of the signals corresponding to each projection yields the spatial distribution of the MR signal due to nuclei throughout the imaging slice. As indicated in connection with FIG. 6, in order to obtain an image depicting only the arterial flow in spatial distribution, two images having different acquisition delays $T_A$ can be subtracted so as to cancel the images that are not affected by the different delays, i.e., stationary and constant flow nuclei. It will be recognized that signal averaging may also be advantageously employed in the foregoing imaging scheme to improve the signal-to-noise ratio.

Figure 8:
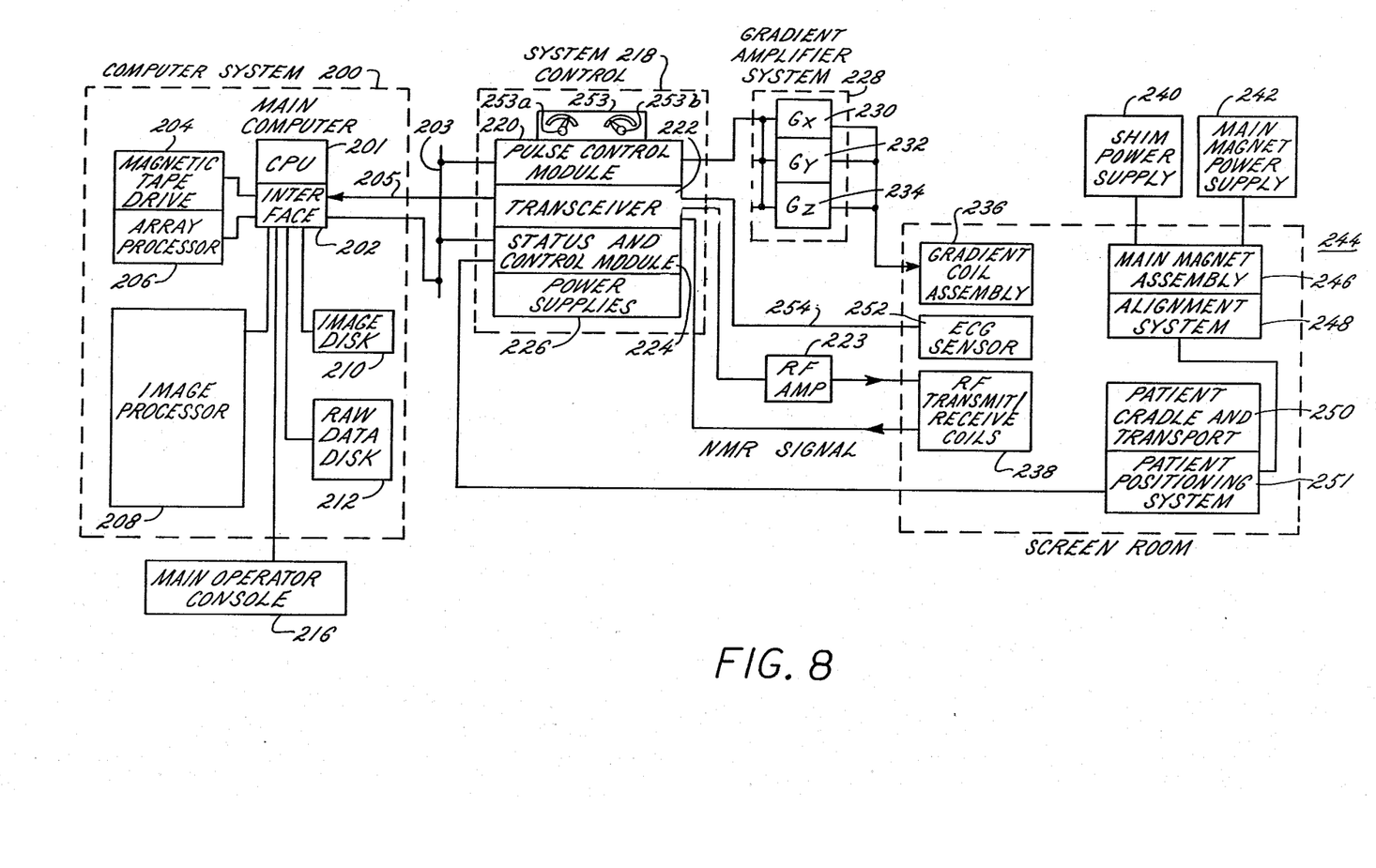
FIG. 8 is a schematic block diagram of the major component elements of a MR system according to the invention.

Referring to FIG. 8, overall system opration is under the control of a computer system generally designated 200 which includes a main computer 201, such as a Data General MV4000. The computer 201 has associated therewith an interface 202 through which a plurality of peripheral devices and other MR system components are coupled. Among the peripheral devices which may be utilized under the direction of the main computer 201 is a magnetic tape drive 204 for archiving patient data and images to magnetic tape. Processed patient data may also be stored in an image disk storage device 210. An array processor 206 is utilized for pre-processing data and data reconstruction. In order to provide interactive image display manipulation such as magnification, image subtraction and gray scale adjustment, an image processor 208 is joined to the main computer 201 via interface 202. The computer system 200 is provided with a means to store raw (unreconstructed) image data utilizing a disk storage system 212. An operator console 216 is also coupled to the computer 201 via the interface 202 and provides the operator with the means to input data pertinent to a patient study as well as additional data necessary for proper MR system operation, such as initiating and terminating scans. The operator console may also include a CRT for displaying images stored on disks or magnetic tape.

Control over the MR system is exercised by means of control and gradient amplifier systems 218 and 228, respectively. The computer 201 communicates with the system control 218 by way of a conventional digital communication network 203 (such as an Ethernet network) in a manner well known to those skilled in the art. A particular system control suitable for the illustrated MR system is that employed by the SIGNA MR system, manufactured by General Electric Company, Medical Systems Group, Milwaukee, Wis. The system control 218 includes several subsystems such as the pulse control module 220 (commonly referred to as PCM), a radio-frequency transceiver 222, a status and control module 224 (commonly referred to as SCM), and the power supplies 226 necessary to energize the components of the system control 218. In response to control signals from the main computer 201, the PCM generates digital timing and control signals such as the current waveforms used for gradient coil excitation, as well as RF envelope waveforms utilized in the transceiver 222 for modulating RF pulses.

The current waveforms from the PCM 220 are applied to the gradient amplifier system 228 generally comprising $G_x$, $G_y$, and $G_z$ amplifiers 230, 232 and 234, respectively. Each amplifier is utilized to excite a corresponding gradient coil in a gradient coil assembly 236. When energized, the gradient coils of the gradient coil assembly 236 generate substantially linear, mutually orthogonal magnetic field gradients $G_x$, $G_y$ and $G_z$ directed in the x, y and z-axis direction, respectively, of a cartesian coordinate system.

In a manner well known to those skilled in the art, the gradient magnetic fields $G_x$, $G_y$ and $G_z$ generated by the gradient coil assembly 236 ae utilized in combination with radio-frequency pulses generated by transceiver 222 to encode spatial information into the MR signals emanating from the region of the patient under study. Waveforms and control signals provided by the PCM 220 are utilized by transceiver 222 for RF carrier modulation and control of the operating mode; that is, the transmit or receive mode. In the transmit mode, the transmitter 222 provides a radio-frequency carrier waveform modulated in accordance with the control signals from the PCM 220 to an RF power amplifier 223 which then energizes RF coils 238 which are physically located inside the main magnet assembly 246. In a receive mode, the RF coils 238 senses the MR signals radiated by the excited nuclei (a separate set of RF coils may be used for the receive mode if desired). The signals are detected, filtered, and digitized in the transceiver 222. The digitized signals are delivered to the main computer 201 for processing by means of a dedicated, unidirectional, high-speed digital link 205 which links interface 202 and transceiver 222.

The gradient coil assembly 236 and the RF transmit and receive coils 238 are mounted within the bore of the magnet in the main magnet assembly 246 utilized to produce the polarizing magnetic field $B_0$. The magnet in the main magnet assembly 246 also surrounds the patient alignment system 248, a shim coil power supply 240 and a main magnet power supply 242. The shim power supply 240 is utilized to energize shim coils (not shown) associated with the main magnet assembly 246 andwwhich are used to correct inhomogeneities in the polarizing magnetic field $B_0$. The patient alignment system 248 operates in combination with a patient cradle and transport system 250 and patient positioning system 251 in a well-known manner.

To minimize interference from external sources, the MR system components including the main magnet assembly 246, the gradient coil assembly 236, and the RF transmit and receive coils 238, as well as the associated power supplies and patient handling devices, are enclosed in an RF-shielded room 244. The shielding is generally provided by a copper or aluminum screen network which enclosed the entire room. The screen network serves to contain the RF signals generated by the system, while shielding the system from RF signals generated outside the room. For isolating the RF signals, a bi-directional attenuation of approximately 80 db in the frequency range of operation, 10 $MH_z$–80 $MH_z$, is appropriate.

In keeping with the invention, the MR system of FIG. 8 includes an ECG sensor 252 within the RF-shielded room 244 for providing an electrocardiogram signal from the patient for use in triggering or gating the pulse sequence. The ECG signal from the ECG sensor 252 supplies to the SCM 224, via the transceiver 222, trigger pulses which synchronize the patient's arterial flow with the scanning time associated with the MR pulse sequence. Preferably, the ECG sensor 252 and the transceiver 222 provide a "R-wave detected" pulse of the ECG signal to the SCM 224. The SCM 224 uses this trigger signal to initiate the pulse sequence at the PCM 220. While diagnostic quality ECG signals are not required, the ECG signal must display a recognizable QRS-complex and give some indication of the R-wave. Therefore, a commercially available sensor of good quality may be used; for example, a possible sensor is Model 78351A, manufactured by Hewlett Packard Company of Waltham, Mass. Of course, the ECG sensor 252 should include a filter arrangement for eliminating interference signals from sources such as the magnetic gradients and/or RF interference.

As with other electrical signals passing through the screen room, the electrical signal from the ECG sensor 252 must pass through an 80 db filter for frequencies between 10 $MH_z$–80 MHz. There should be negligible insertion loss for signal frequencies below 100 hertz. The cable link 254 from the ECG sensor 252 to the system control 218 should be limited in length to 150 feet. For visualization of the ECG signal, a pre-amp (not shown) located inside the ECG sensor 252 may transmit ECG signals to a ECG display (also not shown). The trigger signal from the ECG sensor 252 to the SCM 224 is a R-wave detection pulse (TTL). A timing circuit within the SCM 224 is responsive to the ECG sensor 252 for instituting the acquisition delay $T_A$.

The SCM 224 controls the delay period $T_A$ of its timing circuitry based on the mean heart rate. The delay period $T_A$ may be dynamic such that as the patient's heart rate changes, the delay period reflects that change. The delay period is determined by:

$T_A$ = variable percentage of the mean R-R pulse interval of the QRS-complex where the percentage value depends on the distance from the heart of the slice of tissue to be imaged.

In order to provide adjustability for the delays $T_A$ and $T'_A$, an operator adjustable control 253 includes at least first and second inputs 253a and 253b, respectively. The control 253 provides the timing circuit of the SCM 224 with a predetermined time delay for initiation of the MR pulse sequence after the detection of an R-wave. Inputs 253a and 253b may be rotatable knobs having pointers referenced to scales calibrated as a percentage of a mean cardiac cycle for selecting a percentage of a mean cardiac cycle as the appropriate delay $T_A$ or $T_A'$. It will be appreciated that the delay $T_A$ may often be negligible or, in fact, zero since slow flow may be coincident with the detection of a R-wave. In contrast, the delay $T_A'$ for fast flow imaging will typically have a finite value since propagation of the fast flow is not instantaneous. This delay period is variable within the limits of zero and two seconds and accurate to within two milliseconds.

From the foregoing, it will be appreciated that, in accordance with the invention, an apparatus and method is provided to detect arterial blood flow and to provide a high contrast MR image of the flow. The method is useful in making measurements of flowing blood in MR images for which data may be collected by a variety of MR imaging techniques. While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

I claim:

1. A non-invasive method employing flow-related enhancement MR imaging for identifying flow within an artery of a living body, comprising the steps:
   (a) positioning said body in a substantially homogeneous magnetic field;
   (b) sensing the cardiac cycle of said living body;
   (c) determining a region of said living body for MR imaging including said artery;
   (d) determining from said sensing of the cardiac cycle the times of slow arterial flow in said region;
   (e) tagging a bolus of arterial flow within said region during said times of slow arterial flow;
   (f) exciting said region after waiting a predetermined time period $T_I$ after each tagging of step (e), where time period $T_I$ is sufficient for spins to enter the imaging slice between tagging and excitation wherein the velocity of the flow throughout the time period remains substantially constant;
   (g) detecting first MR signals from said body responsive to the taggings and excitations in steps (e) and (f) which is enhanced by the arterial flow; and
   (h) creating first imaging data from the detected first MR signals.

2. A non-invasive method as set forth in claim 1 including the steps of:
   (i) determining from said sensing of the cardiac cycle the times of fast arterial flow in said region;
   (j) tagging a bolus of arterial flow within said region during said times of fast arterial flow;
   (k) exciting said region after waiting said predetermined time period $T_I$ after each tagging of step (j);
   (l) detecting second MR signals from said body responsive to said taggings and excitations in steps (j) and (k) which is less enhanced by the arterial flow through the region than the first MR signals; and
   (m) creating second imaging data fromm the detected second MR signals.

3. A non-invasive method as set forth in claim 2, including the step of:
   (n) subtracting said first and second imaging data to provide imaging data for a single image of only arterial flow.

4. A non-invasive method as set forth in claim 1 wherein the time between the sensing of the cardiac cycle in step (b) and tagging a bolus of arterial flow in step (e) is a constant percentage of the mean time period of the cardiac cycle.

5. A method for providing a high contrast MR image of arterial flow in living tissue using time-of-flight MR methods wherein the slice of tissue to be iamged is composed of a number of small volume elements of voxels, said method comprising the sequential steps of:
   (a) sensing the period of cyclic arterial flow velocity;
   (b) generating a first MR signal at a first time location corresponding to a time of slow flow within the period of cyclic arterial flow velocity;
   (c) generating a second MR signal at a second time location corresponding to a time of fast flow within the period of cyclic arterial flow velocity;
   (d) repeating steps (a), (b) and (c) to provide two full data sets for each voxel;
   (e) forming a MR image from each of said data sets; and
   (f) comparing said MR images to determine the arterial flow as represented by relatively enhanced areas in the images.

6. A method as set forth in claim 5, including the step of:
   (g) combining the image data of the two images to provide a single image wherein image data from stationary voxels and voxels of constant flow are cancelled, leaving only net image data for voxels representing arterial flow.

7. A non-invasive method employing MR for identifying flow within an artery of a living body, comprising the steps of:
   (a) positioning said body in a substantially homogeneous magnetic field;
   (b) sensing the cardiac cycle of said living body;
   (c) determining a slice of said living body for MR imaging including said artery;
   (d) determining the propagation delay from the start of a cardiac cycle, marked by a contraction of the heart, to the occurrence of a predetermined arterial flow condition in the slice to be images;
   (e) generating and detecting MR signals in said slice at two predetermined temporal locations of a cardiac cycle utilizing a flow-related enhancement method which is time adjsuted by an amount approximately equal to said propagation delay so as to accurately reflect the arterial flow rate in said slice during generation and detection of said MR signal;
   (f) creating imaging data from detected MR siganls for each temporal location; and
   (g) subtracting imaging data associated with one temporal location from the imaging data associated with the other temporal location.

8. A non-invasive method as set forth in claim 7 wherein a first one of said predetermined temporal locations occurs during slow arterial flow and a second one of said predetermined temporal locations occurs during fast arterial flow.

9. A non-invasive method as set forth in claim 7 wherein the step of generating and detecting MR signals at one of said two predetermined temporal locations comprises the steps of:
   (h) tagging a bolus of arterial flow within the slice before the occurrence of said predetermined arterial flow condition within the slice; and
   (i) waiting a predetermined time period $T_I$ and then exciting a bolus of arterial flow in the slice so as to generate MR signals at said one of said two predetermined temporal locations.

10. A method for enhancing arterial flow in an MR image of a slice of living tissue, said method comprising the steps of:
    (1) generating a homogenous magnetic field through living tissue which includes said slice;
    (2) determining the cycle of said arterial flow associated with said living tissue;
    (3) generating a first series of RF pulses sequences for sequentially tagging and exciting selected new nuclei in said slice such that each of said RF pulse sequences in said first series is synchronized with said cycle of arterial flow so as to be initiated after the expiration of a first time delay related to the propagation delay of said cycle of arterial flow from an area of its determination to said slice;
    (4) adjusting the value of said first time delay such that any MR signal from the excited nuclei in said occurs during a time of slow arterial flow in the slice;
    (5) collecting the MR signals from said excited nuclei in said slice; and (6) creating imaging data from the MR signals collected in step (5).

11. A method as set forth in claim 10 including the steps of:

(7) generating a second series of RF pulse sequences for sequentially tagging and exciting selected nuclei in said slice such that each of said RF pulse sequences in said second series is synchronized with said cycle of arterial flow so as to be initiated after the expiration of a second time delay related to the propagation delay of said cycle of arterial flow from an area of its determination to said slice;

(8) collecting any MR signals from said excited nuclei in said slice;

(9) creating imaging data from the MR signals collected in step (8).

12. A method as set forth in claim 11 including the step of:

(10) adjusting the value of said second time delay such that the MR signals from the excited nuclei in said slice occur during times of fast arterial flow in the slice.

13. A method as set forth in claim 12 wherein step (4) includes determining the mean time period of the arterial flow cycle and for allowing adjustment of said first and second time delays as percentages of said mean time period.

14. A method as set forth in claim 13 including the step of:

(11) subtracting imaging data geneated from said second series of RF pulse sequences from imaging data generated from said first series of RF pulse sequences.

* * * * *